(12) United States Patent
Boiteau et al.

(10) Patent No.: US 8,119,674 B2
(45) Date of Patent: *Feb. 21, 2012

(54) 4-PHENYLIMIDAZOLE-2-THIONE TYROSINASE INHIBITORS AND PHARMACEUTICAL/COSMETIC APPLICATIONS THEREOF

(75) Inventors: Jean-Guy Boiteau, Valbonne (FR); Corinne Millois Barbuis, Saint Raphael (FR); Sandrine Talano, Vence (FR)

(73) Assignee: Galderma Research & Development, Biot (FR)

( * ) Notice: Subject to any disclaimer, the term of this patent is extended or adjusted under 35 U.S.C. 154(b) by 60 days.

This patent is subject to a terminal disclaimer.

(21) Appl. No.: 12/631,392

(22) Filed: Dec. 4, 2009

(65) Prior Publication Data

US 2010/0144814 A1 Jun. 10, 2010

Related U.S. Application Data

(63) Continuation of application No. PCT/FR2008/050994, filed on Jun. 4, 2008.

(30) Foreign Application Priority Data

Jun. 5, 2007 (FR) ..................................... 07 55470

(51) Int. Cl.
*A61K 31/4164* (2006.01)
*C07D 233/42* (2006.01)
(52) U.S. Cl. ..................................... 514/386; 548/316.4
(58) Field of Classification Search ............... 548/316.4; 514/386
See application file for complete search history.

(56) References Cited

FOREIGN PATENT DOCUMENTS

| JP | 05124923 | 5/1993 |
|----|----------|--------|
| JP | 05132422 | 5/1993 |
| WO | WO 2007/039821 A2 | 4/2007 |

OTHER PUBLICATIONS

U.S. Appl. No. 12/631,450, commonly assigned to Galderma et al, filed Dec. 2009.*
Mor et al, J. Med. Chem (1997), vol. 40, pp. 2571-2578.*
Lawson et al., "2-Mercaptoglyoxalines. Part XI. The Preparation of Mixed 1:5 Disubstituted 2-Mercaptoglyoxalines and the Corresponding Thiazole (3':2:1) glyoxalines", Journal of Chemical Society, 1956, pp. 566-568, London, GB.
Mor et al., H3-Receptor Antagonists: Synthesis and Structure-Activity Relationships of Para- and Meta-Substituted 4(5)-Phenyl-2-[[2[4(5)-imidazolygethyl]thio]imidazoles, J. Med. Chem., 1997, pp. 2571-2578, vol. 40, American Chemical Society.

\* cited by examiner

*Primary Examiner* — Kamal Saeed
*Assistant Examiner* — Janet L Coppins
(74) *Attorney, Agent, or Firm* — Buchanan Ingersoll & Rooney PC (57) ABSTRACT

Novel 4-phenylimidazole-2-thione tyrosinase inhibiting compounds corresponding to the following general formula (I):

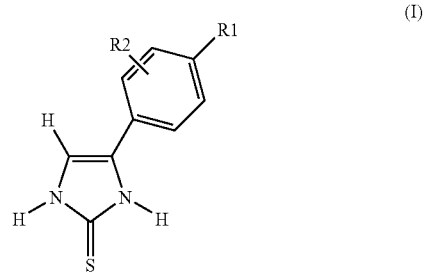

formulated into pharmaceutical or cosmetic compositions are useful for the treatment or prevention of pigmentary disorders, or for preventing and/or treating signs of skin aging, and/or for body or hair hygiene.

16 Claims, 1 Drawing Sheet

Figure 1 : Method A

Figure 2 : Method B

4-PHENYLIMIDAZOLE-2-THIONE TYROSINASE INHIBITORS AND PHARMACEUTICAL/COSMETIC APPLICATIONS THEREOF

CROSS REFERENCE TO PRIORITY/PCT APPLICATIONS

This application claims priority under 35 U.S.C. §119 of FR 0755470, filed Jun. 5, 2007, and is a continuation of PCT/FR 2008/050994, filed Jun. 4, 2008 and designating the United States (published in the French language on Dec. 18, 2008 as WO 2008/152331 A1; the title and abstract were also published in English), each hereby expressly incorporated by reference in its entirety and each assigned to the assignee here hereof.

BACKGROUND OF THE INVENTION

1. Technical Field of the Invention

The present invention relates to novel 4-phenylimidazole-2-thione compounds as industrial and useful products. It also relates to their process of preparation and to their formulation, as tyrosinase inhibitors, into pharmaceutical or cosmetic compositions useful for the treatment or prevention of pigmentary disorders.

2. Description of Background and/or Related and/or Prior Art

The pigmentation of the skin, in particular human skin, results from the synthesis of melanin by the dendritic cells, the melanocytes. The melanocytes comprise organelles, known as melanosomes, which transfer the melanin into the upper layers of keratinocytes, which are then transported to the surface of the skin via the differentiation of the epidermis.

Among the enzymes of melanogenesis, tyrosinase is a key enzyme which catalyzes the first two stages of the synthesis of melanin. Homozygous tyrosinase mutations result in oculocutaneous albinism type I characterized by a complete absence of the synthesis of melanin.

It is proving to be important to develop novel therapeutic approaches to treat disorders of pigmentation resulting from an increase in the production of melanin, for which there exists no treatment satisfying all the expectations of patients and dermatologists.

The majority of skin-lightening compounds already known are phenols/catechols. These compounds inhibit tyrosinase but the majority of them are cytotoxic for the melanocytes as a result of oxidation phenomenon resulting in the formation of quinones responsible for this toxicity. This toxic effect risks bringing about permanent depigmentation of the skin.

SUMMARY OF THE INVENTION

It has now unexpectedly and surprisingly been discovered that novel compounds with the 4-phenylimidazole-2-thione structure exhibit a very good inhibitory activity for the enzyme tyrosinase and a very low cytotoxicity.

These compounds find applications in human medicine, in particular in dermatology, and in the field of cosmetics.

Among the imidazole-2-thione derivatives already known, some have been described as having anti-inflammatory properties (S. Maeda, M. Suzuki, T. Iwasaki, K. Matsumoto and Y. Iwazawa, *Chem. Pharm. Bull.,* 1984, 32, 7, 2536-2543).

Others have been reported in U.S. Pat. No. 4,798,843 to be inhibitors of dopamine β-hydroxylase. The compounds described in this patent are effective in preventing gastric ulcers.

Other imidazole-2-thiones are also described as reaction intermediates in the synthesis of H3 receptor antagonists (M. Mor, F. Bordi, C. Silva, S. Rivara, P. Crivori, P. V. Plazzi, V. Ballabeni, A. Caretta, E. Barocelli, M. Impicciatore, P.-A. Carrupt and B. Testa, *J. Med. Chem.,* 1997, 40, 2471-2578).

Yet others have been described in WO 2006/019962 as TLR and TNR-α modulators. In this patent publication, the claimed compounds are useful in the treatment of IBD (inflammatory bowel disease) and gastrointestinal pathologies.

EP-131,973 also teaches the administration of certain compounds derived from imidazole-2-thiones as gastric acid secretion inhibitors that are useful in the treatment of ulcers.

JP05132422 discloses the administration of certain imidazole-2-thiones as tyrosinase inhibitors. However, no imidazole-2-thione derivative substituted in the 4 position by an aryl moiety is described. No inhibitory activity for tyrosinase is shown for compounds with the 4-arylimidazole-2-thione structure. In point of fact, it has now unexpectedly and surprisingly been found that certain compounds with the 4-phenylimidazole-2-thione structure according to the present invention exhibit an inhibitory activity for tyrosinase which is much better than that of the compounds of JP05132422.

Thus, the present invention features novel compounds of the following general formula (I):

$$\text{(I)}$$

[structure of 4-phenylimidazole-2-thione with R1 and R2 substituents on the phenyl ring]

in which:
a) when R2=H, then R1 is:
  a $C_2$-$C_7$ alkyl radical, with the exception of isopropyl, n-propyl and tert-butyl,
  a hydroxymethyl, trifluoromethoxy or difluoromethoxy radical,
  a $C_3$-$C_7$ cycloalkyl radical, with the proviso that one of the carbon atoms of the ring may optionally be replaced by an oxygen or sulfur atom,
  a $C_4$-$C_9$ cycloalkylalkyl radical,
  a morpholinyl, thiomorpholinyl, piperazinyl or N-methylpiperazinyl group,
  a carboxyl substituent,
  a ($C_1$-$C_4$ alkoxy)carbonyl group, or
  a $C_2$-$C_6$ alkoxy radical, with the exception of n-butoxy,
b) when R1=H, then R2 is:
  a $C_1$-$C_7$ alkyl radical,
  a trifluoromethoxy, difluoromethoxy or cyano radical,
  a $C_3$-$C_7$ cycloalkyl radical, with the proviso that one of the carbon atoms of the ring may optionally be replaced by an oxygen or sulfur atom,
  a $C_4$-$C_9$ cycloalkylalkyl radical,
  a ($C_1$-$C_4$ alkoxy)carbonyl radical,
  a $C_1$-$C_6$ alkoxy radical, with the exception of n-propoxy,
c) and, when R2 is in the ortho position with respect to R1, then R1 and R2, which may be identical or different, are each a $C_1$-$C_5$ alkyl radical or can together form a 5- or 6-sided hydrocarbon ring, with the proviso that 1 or 2 carbon atom(s) can optionally be replaced by 1 or 2 oxygen atom(s),
and their salts and tautomeric forms thereof.

More particularly, the present invention relates to compounds of general formula (I) as defined above in which, when R2 is in the ortho position with respect to R1, then R1 and R2, which may be identical or different, are each a $C_1$-$C_5$ alkyl radical or can form a 5- or 6-sided hydrocarbon ring in which 1 or 2 carbon atom(s) can optionally be replaced by 1 or 2 oxygen atom(s).

More particularly, the present invention relates to compounds as defined above, wherein, when R2 is in the ortho position with respect to R1, then R1 and R2, which may be identical or different, are each a $C_1$-$C_5$ alkyl radical or can form a 5- or 6-sided hydrocarbon ring.

The present invention also relates to the formulation of the compounds of formula (I) as defined above, or their salts or their tautomeric forms thereof, into pharmaceutical compositions useful for the treatment or prevention of hyperpigmentary disorders.

DETAILED DESCRIPTION OF BEST MODE AND SPECIFIC/PREFERRED EMBODIMENTS OF THE INVENTION

The tautomeric forms can be represented as follows:

Preferred are, among the addition salts of the compounds of general formula (I) with a pharmaceutically acceptable acid, the salts with an organic acid or with an inorganic acid.

The appropriate inorganic acids are, for example, hydrohalic acids, such as hydrochloric acid or hydrobromic acid, sulfuric acid or nitric acid.

The appropriate organic acids are, for example, picric acid, methanesulfonic acid, ethanesulfonic acid or trifluoromethanesulfonic acid.

The compounds of general formula (I) can also exist in the form of hydrates or of solvates with water or with a solvent.

The appropriate solvents for forming solvates or hydrates are, for example, alcohols, such as ethanol or isopropanol, or water.

According to the present invention, $C_3$-$C_7$ cycloalkyl is a saturated cyclic hydrocarbon chain having from 3 to 7 carbon atoms. Preferably, the $C_3$-$C_7$ cycloalkyl radical is selected from the cyclopropyl, cyclobutyl, cyclopentyl, cyclohexyl and cycloheptyl radicals.

According to the present invention, $C_1$-$C_7$ alkyl is a saturated and linear or branched hydrocarbon chain having from 1 to 7 carbon atoms. Preferably, the $C_1$-$C_7$ alkyl radical is selected from the methyl, ethyl, propyl, isopropyl, butyl, t-butyl, pentyl, hexyl and heptyl radicals.

According to the present invention, $C_2$-$C_7$ alkyl is a saturated and linear or branched hydrocarbon chain having from 2 to 7 carbon atoms. Preferably, the $C_2$-$C_7$ alkyl radical is selected from the ethyl, propyl, isopropyl, butyl, t-butyl, pentyl, hexyl and heptyl radicals.

According to the present invention, $C_4$-$C_9$ cycloalkylalkyl is a saturated and linear or branched hydrocarbon chain substituted by a cycloalkyl radical and having from 4 to 9 carbon atoms. Preferably, the $C_4$-$C_9$ cycloalkylalkyl radical is selected from the cyclopropylmethyl, cyclopropylethyl, cyclobutylmethyl, cyclobutylethyl, cyclopentylmethyl, cyclopentylethyl, cyclohexylmethyl and cyclohexylethyl radicals.

According to the present invention, ($C_1$-$C_4$ alkoxy)carbonyl is a carboxyl radical substituted by a saturated and linear or branched hydrocarbon chain having from 1 to 4 carbon atoms. Preferably, the ($C_1$-$C_4$ alkoxy)carbonyl radical is selected from the methoxycarbonyl, ethoxycarbonyl, propoxycarbonyl and butoxycarbonyl radicals.

According to the present invention, $C_2$-$C_6$ alkoxy is an oxygen atom substituted by a saturated and linear or branched hydrocarbon chain having from 2 to 6 carbon atoms. Preferably, the $C_2$-$C_6$ alkoxy radical is selected from the ethoxy, propoxy, butoxy, pentoxy and hexyloxy radicals.

According to the present invention, $C_1$-$C_6$ alkoxy is an oxygen atom substituted by a saturated and linear or branched hydrocarbon chain having from 1 to 6 carbon atoms. Preferably, the $C_1$-$C_6$ alkoxy radical is selected from the methoxy, ethoxy, propoxy, butoxy, pentoxy and hexyloxy radicals.

According to the present invention, the compounds of general formula (I) which are particularly preferred are those in which:
R2 is a hydrogen atom, and
R1 is a $C_2$-$C_7$ alkyl radical, with the exception of isopropyl, n-propyl and tert-butyl, or a $C_3$-$C_7$ cycloalkyl radical or a $C_4$-$C_9$ cycloalkylalkyl radical. According to the present invention, the compounds of general formula (I) which are more particularly preferred are those in which:
R1 is a hydrogen atom, and
R2 is a $C_1$-$C_7$ alkyl radical, a $C_3$-$C_7$ cycloalkyl radical or a $C_4$-$C_9$ cycloalkylalkyl radical.

Among the compounds of formula (I) according to the present invention, the following compounds are particularly exemplary:
4-(4-pentylphenyl)-1,3-dihydroimidazole-2-thione,
4-(3-carboxyphenyl)-1,3-dihydroimidazole-2-thione;
4-(4-carboxyphenyl)-1,3-dihydroimidazole-2-thione;
4-(4-cyclohexylphenyl)-1,3-dihydroimidazole-2-thione;
4-(4-(N-morpholin-4-yl)phenyl)-1,3-dihydroimidazole-2-thione;
methyl 4-(2-thioxo-2,3-dihydro-1H-imidazol-4-yl)benzoate;

4-(4-(hydroxymethyl)phenyl)-1,3-dihydroimidazole-2-thione,
4-(4-(trifluoromethoxy)phenyl)-1,3-dihydroimidazole-2-thione;
4-(4-(difluoromethoxy)phenyl)-1,3-dihydroimidazole-2-thione;
4-(3-butoxyphenyl)-1,3-dihydroimidazole-2-thione;
4-(3-methoxyphenyl)-1,3-dihydroimidazole-2-thione;
4-(2-methylphenyl)-1,3-dihydroimidazole-2-thione;
4-(2-methoxyphenyl)-1,3-dihydroimidazole-2-thione;
4-(3-methylphenyl)-1,3-dihydroimidazole-2-thione;
4-(3-(trifluoromethoxy)phenyl)-1,3-dihydroimidazole-2-thione;
3-(2-thioxo-2,3-dihydro-1H-imidazol-4-yl)benzonitrile;
4-(4-isobutylphenyl)-1,3-dihydroimidazole-2-thione;
4-(4-ethylphenyl)-1,3-dihydroimidazole-2-thione;
4-(3-ethylphenyl)-1,3-dihydroimidazole-2-thione;
4-(3,4-dimethylphenyl)-1,3-dihydroimidazole-2-thione;
4-(4-cyclopentylphenyl)-1,3-dihydroimidazole-2-thione;
4-(3-cyclopentylphenyl)-1,3-dihydroimidazole-2-thione;
4-(3-cyclohexylphenyl)-1,3-dihydroimidazole-2-thione;
4-(5,6,7,8-tetrahydronaphth-2-yl)-1,3-dihydroimidazole-2-thione;
4-(indan-5-yl)-1,3-dihydroimidazole-2-thione,
4-(2,3-dihydrobenzofuran-5-yl)-1,3-dihydroimidazole-2-thione;
4-(2,3-dihydrobenzo[1,4]dioxin-6-yl)-1,3-dihydroimidazole-2-thione;
4-(benzo[1,3]dioxol-5-yl)-1,3-dihydroimidazole-2-thione;
4-[4-(tetrahydropyran-4-yl)phenyl]-1,3-dihydroimidazole-2-thione;
4-[3-(tetrahydropyran-4-yl)phenyl]-1,3-dihydroimidazole-2-thione;
4-(3,4-diethylphenyl)-1,3-dihydroimidazole-2-thione;
4-(3-ethyl-4-isopropylphenyl)-1,3-dihydroimidazole-2-thione;
4-(4-ethyl-3-isobutylphenyl)-1,3-dihydroimidazole-2-thione; and
4-(3,4-diethylphenyl)-1,3-dihydroimidazole-2-thione hydrochloride.

BRIEF DESCRIPTION OF THE DRAWINGS

The compounds of general formula (I) are prepared according to the general reaction schemes presented in FIG. 1 and in FIG. 2.

Figure 1:
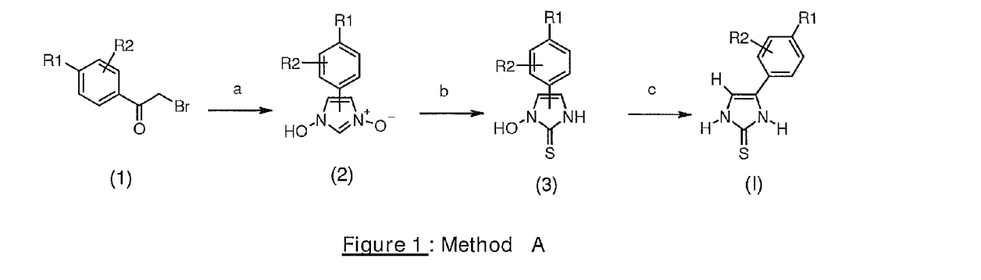

Employing the reaction scheme of FIG. 1 (Method A, stage a), α-bromoketones of general formula (1):

commercially available or prepared according to conventional synthetic methods (W. D. Langley, Org. Synth. I, 122 (1932)), are reacted with oxidizing agents, such as pyridine N-oxide, for example, to result in the corresponding intermediate glyoxals (Chandrasekhar S, and Sridhar M., Tetrahedron Lett., 2000, 41 (28), 5423-5425). A cyclization reaction using formaldehyde and hydroxylamine is carried out on the crude reaction product in an acidic medium to give the compounds of general formula (2) (Akagane K. and Allan G. G., Chem. Ind. (London), 1974, 38).

The compounds of general formula (2) react (stage b) with thioadamantanone, for example, to result in the compounds of general formula (3) (Mloston G., Gendek T. and Heimgartner H., Helv. Chim. Acta, 1998, 81 (9), 1585-1595).

The compounds of general formula (I) are obtained from the compounds of general formula (3) by reduction with a solution of titanium(III) chloride, for example (Mattingly P. G. and Miller M. J., J. Org. Chem., 1980, 45 (3), 410).

Figure 2:
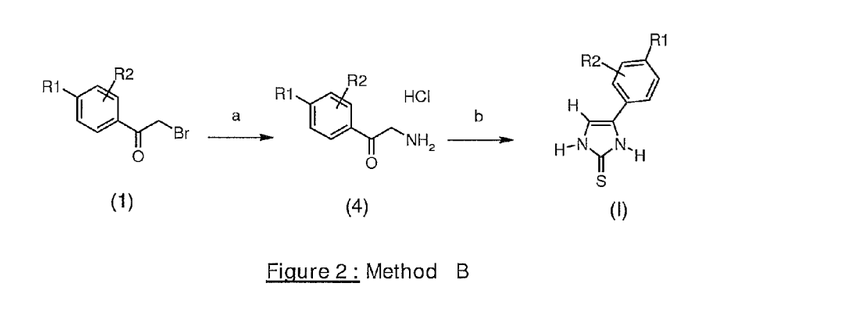

Employing the reaction scheme of FIG. 2 (Method B: stage a), α-bromoketones of general formula (1):

are reacted with sodium diformylamide, for example, in acetonitrile (Yinglin H. and Hongwen H., Synthesis, 1990, 615), to give, after hydrolysis of the crude reaction product with hydrochloric acid, for example (Ying-Lin H. and Hong-Wen H. H., Tetrahedron Lett., 1989, 30, 5285), the acylamine hydrochlorides of general formula (4):

A cyclization reaction (stage b) of the compounds of general formula (4) using potassium thiocyanate provides the imidazole-2-thiones of general formula (I) (Mor M., Bordi F., Silva C., Rivara S., Crivori P., Plazzi P. V., Ballabeni V., Caretta A., Barocelli E., Impicciatore M., Carrupt P.-A. and Testa B., *J. Med. Chem.*, 1997, 40 (16), 2571-2578).

Advantageously, the compounds of the present invention exhibit an $IC_{50}$ (dose which inhibits 50% of the enzymatic activity) value with regard to tyrosinase of less than or equal to 10 µM and more particularly of less than or equal to 1 µM.

This invention therefore features formulation of at least one compound of general formula (I) into pharmaceutical or cosmetic compositions exhibiting tyrosinase-inhibiting activity.

This invention also features administration of the compounds of formula (I) for the treatment and/or prevention of pigmentary disorders.

The present invention also features therapeutic or cosmetic treatment regime or regime comprising the administration, as tyrosinase inhibitor, of a pharmaceutical or cosmetic composition comprising the said compounds of formula (I).

The present invention also features the formulation of a compound of general formula (I) into medicaments useful for the treatment of pigmentary disorders, in particular hyperpigmentary disorders.

This because the compounds according to the invention are particularly appropriate for the treatment and/or prevention of pigmentary disorders, such as melasma, chloasma, lentigines, senile lentigo, irregular hyperpigmentations related to photoaging, freckles, postinflammatory hyperpigmentations due to an abrasion and/or a burn and/or a scar and/or a dermatosis and/or a contact allergy; naevi, genetically determined hyperpigmentations, hyperpigmentations of metabolic or drug origin, melanomas or any other hyperpigmentary lesion.

Another aspect of the present invention is a pharmaceutical composition useful in particular for the treatment of the abovementioned conditions which comprises, formulated into a pharmaceutically acceptable vehicle compatible with the method of administration selected for the composition, at least one compound of general formula (I) in one of its tautomeric forms or at least one of its salts with a pharmaceutically acceptable acid.

"Pharmaceutically acceptable vehicle" means a medium compatible with the skin, mucous membranes and superficial body growths.

The compositions according to the invention can be administered topically. Preferably, the pharmaceutical composition is packaged in a form suitable for application topically. Topically means administration to the skin or mucous membranes.

The pharmaceutical compositions according to the invention are administered topically, more particularly for the treatment of the skin and mucous membranes and can be provided in the liquid, pasty or solid form and more particularly in the form of ointments, creams, milks, salves, powders, impregnated pads, syndets, solutions, gels, sprays, foams, suspensions, sticks, shampoos or washing bases. Same can also be provided in the form of suspensions of microspheres or nanospheres or of lipid or polymeric vesicles or of polymeric or gelled patches which make possible controlled release.

The compositions for topical application have a concentration of compound according to the invention generally ranging from 0.001% to 10% by weight, preferably from 0.01% to 5% by weight, with respect to the total weight of the composition.

The compounds of general formula (I) according to the invention also find application in the cosmetics field, in particular for protecting against the harmful aspects of the sun, for preventing and/or combating photoinduced or chronological aging of the skin and superficial body growths.

Another aspect of the invention is thus cosmetic compositions comprising, in a cosmetically acceptable vehicle, at least one compound of general formula (I). "Cosmetically acceptable vehicle" means a medium compatible with the skin, mucous membranes and superficial body growths.

Another aspect of the invention is the cosmetic application of a compound of formula (I) or of a composition comprising at least one compound of general formula (I) for preventing and/or treating the signs of skin aging.

Another aspect of the invention is the cosmetic application of a compound of formula (I) or of a composition comprising at least one compound of general formula (I) for body or hair hygiene.

The cosmetic compositions according to the invention comprising, in a cosmetically acceptable vehicle, a compound of general formula (I) or one of its tautomeric forms or one of its salts with a pharmaceutically acceptable acid can be provided in particular in the form of a cream, a milk, a gel, suspensions of microspheres or nanospheres or lipid or polymeric vesicles, impregnated pads, solutions, sprays, foams, sticks, soaps, washing bases or shampoos.

The concentration of compound of general formula (I) in the cosmetic composition preferably ranges from 0.001% to 3% by weight, with respect to the total weight of the composition.

The pharmaceutical and cosmetic compositions as described above can additionally comprise inert additives or even pharmacodynamically active additives, as regards the pharmaceutical compositions, or combinations of these additives, and in particular:

wetting agents;

flavor enhancers;

preservatives, such as para-hydroxybenzoic acid esters;

stabilizers;

moisture regulators;

pH-regulating agents;

osmotic pressure modifiers;

emulsifying agents;

UV-A and UV-B screening agents;

antioxidants, such as α-tocopherol, butylated hydroxyanisole or butylated hydroxytoluene, superoxide dismutase or ubiquinol;

emollients;

moisturising agents, such as glycerol, PEG 400, thiamorpholinone and its derivatives, or urea;

antiseborrhoeic or antiacne agents, such as S-carboxymethylcysteine, S-benzylcysteamine, their salts or their derivatives, or benzoyl peroxide.

Of course, one skilled in the art will take care to select the optional compound or compounds to be added to these compositions such that the advantageous properties intrinsically associated with the present invention are not, or not substantially, detrimentally affected by the envisaged addition.

To further illustrate the present invention and the advantages thereof, the following specific examples are given, including those indicating biological activity, it being understood that same are intended only as illustrative and in nowise limitative. In said examples to follow, all parts and percentages are given by weight, unless otherwise indicated.

Method A.

Example 1

4-(4-Pentylphenyl)-1,3-dihydroimidazole-2-thione (Method A)

3-Oxy-(4,5)-(4-pentylphenyl)imidazol-1-ol 7 g (74 mmol, 2 eq) of pyridine N-oxide are added at 0° C. to a solution of 10 g (37 mmol, 1 eq) of commercial 2-bromo-1-(4-pentylphenyl)ethanone in 100 ml of methanol. The reaction mixture is stirred at ambient temperature for 48 hours. 4.2 ml (55.5 mmol, 1.5 eq) of a 37% formaldehyde solution are added and also a solution of 5.6 g of hydroxylamine hydrochloride in 12 ml of water. 4 ml of concentrated hydrochloric acid are added dropwise and then the reaction mixture is stirred at ambient temperature for 48 hours. The reaction mixture is then neutralized (pH=5) with a sodium hydroxide solution. The precipitate formed is filtered off and then rinsed with diethyl ether. 6.4 g of 3-oxy-(4,5)-(4-pentylphenyl)imidazole-1-ol are obtained in the form of a beige powder.

Yield=70%.

$^1$H NMR ($d_6$-DMSO, 1 drop of $D_2O$, 400 MHz): 0.86 (t, 3H, J=7 Hz, $CH_3$); 1.30 (m, 4H, $CH_2$); 1.60 (m, 2H, $CH_2$); 2.63 (t, 2H, J=7 Hz, $CH_2$); 7.33 (d, 2H, J=8 Hz, ArH); 7.70 (d, 2H, J=8 Hz, ArH); 8.13 (s, 1H, CH); 9.78 (s, 1H, CH).

1-Hydroxy-(4,5)-(4-pentylphenyl)-1,3-dihydroimidazole-2-thione

A suspension of 2 g (12.1 mmol, 1.5 eq) of thioadamantanone in 4 ml of dichloromethane is added at ambient temperature to a suspension of 2 g (8.1 mmol, 1 eq) of 3-oxy-(4,5)-(4-pentylphenyl)imidazole-1-ol in 20 ml of methanol. The reaction mixture is stirred at ambient temperature for 18 hours. The precipitate formed is filtered off and then the filtrate is evaporated. The solid obtained is recrystallized from a heptane/ethanol mixture: 1.1 g of white powder comprising the two 1-hydroxy-(4,5)-(4-pentylphenyl)-1,3-dihydroimidazole-2-thione isomers are collected.

Yield=53%

$^1$H NMR ($d_6$-DMSO, 400 MHz): 0.83 (t, 3H, J=7 Hz, $CH_3$); 1.30 (m, 4H, $CH_2$); 1.57 (m, 2H, $CH_2$); 2.55 (t, 2H, J=7 Hz, $CH_2$); 7.13+7.71 (2s, 1H, CH); 7.19+7.23 (2d, 2H, J=8 Hz, ArH); 7.55+7.58 (2d, 2H, J=8 Hz, ArH); 11.5+11.7 (2s, 1H, OH); 12.3+12.6 (2s, 1H, NH).

4-(4-Pentylphenyl)-1,3-dihydroimidazole-2-thione 2.7 ml (7.18 mmol, 2 eq) of a 30% solution of titanium trichloride in 2N hydrochloric acid are added at ambient temperature to 0.9 g of the preceding mixture in 50 ml of methanol. The reaction medium is stirred at ambient temperature for 16 hours. The mixture is basified with a 2N sodium hydroxide solution and then extracted with ethyl acetate. The organic phase is washed with a saturated sodium chloride solution, dried over sodium sulfate and evaporated. 450 mg of 4-(4-pentylphenyl)-1,3-dihydroimidazole-2-thione are obtained.

Yield=53%

$^1$H NMR ($d_6$-DMSO, 400 MHz): 0.83 (t, 3H, J=7 Hz, $CH_3$); 1.30 (m, 4H, $CH_2$); 1.57 (m, 2H, $CH_2$); 2.55 (t, 2H, J=7 Hz, $CH_2$); 7.19 (d, 2H, J=8 Hz, ArH); 7.33 (s, 1H, CH); 7.57 (d, 2H, J=8 Hz, ArH); 12.1 (s, 1H, NH); 12.5 (s, 1H, NH).

$^{13}$C NMR ($d_6$-DMSO, 100 MHz): 17.6, 25.6, 34.1, 34.5, 38.4, 115.2, 127.5, 129.5, 132.3, 132.8, 145.2, 165.0.

The following compounds were obtained analogously to Example 1.

Example 2

4-(3-Carboxyphenyl)-1,3-dihydroimidazole-2-thione (Method A)

$^1$H NMR ($d_6$-DMSO, 400 MHz): 7.51 (m, 2H, CH & ArH); 7.80 (d, 1H, J=8 Hz, ArH); 7.91 (d, 1H, J=8 Hz, ArH); 8.26 (s, 1H, ArH); 12.2 (s, 1H, NH); 12.7 (s, 1H, NH); 13.2 (s, 1H, COOH).

$^{13}$C NMR ($d_6$-DMSO, 100 MHz): 116.8, 128.4, 131.6, 131.7, 131.8, 132.4, 132.8, 135.2, 165.6, 170.7.

Example 3

4-(4-Carboxyphenyl)-1,3-dihydroimidazole-2-thione (Method A)

$^1$H NMR ($d_6$-DMSO, 400 MHz): 7.60 (s, 1H, CH); 7.80 (d, 2H, J=8 Hz, ArH); 7.95 (d, 2H, J=8 Hz, ArH); 12.3 (s, 1H, NH); 12.7 (s, 1H, NH); 13.0 (s, 1H, COOH).

$^{13}$C NMR ($d_6$-DMSO, 100 MHz): 118.0, 127.3, 131.76, 132.6, 133.5, 136.0, 166.1, 170.5.

Example 4

4-(4-Cyclohexylphenyl)-1,3-dihydroimidazole-2-thione (Method A)

$^1$H NMR ($d_6$-DMSO, 400 MHz): 1.37 (m, 4H, $CH_2$); 1.76 (m, 6H, $CH_2$); 2.48 (m, 1H, CH); 7.21 (d, 2H, J=8 Hz, ArH); 7.32 (s, 1H, CH); 7.58 (d, 2H, J=8 Hz, ArH); 12.1 (s, 1H, NH); 12.5 (s, 1H, NH).

$^{13}$C NMR ($d_6$-DMSO, 100 MHz): 25.9, 26.6, 34.2, 43.8, 111.9, 124.4, 126.1, 127.6, 129.8, 147.5, 161.3.

Example 5

4-(4-(N-morpholin-4-yl)phenyl)-1,3-dihydroimidazole-2-thione (Method A)

$^1$H NMR ($d_6$-DMSO, 400 MHz): 3.13 (m, 4H, $CH_2$); 3.74 (m, 4H, $CH_2$); 6.95 (d, 2H, J=8 Hz, ArH); 7.21 (s, 1H, CH); 7.54 (d, 2H, J=8 Hz, ArH); 12.0 (s, 1H, NH); 12.3 (s, 1H, NH).

$^{13}$C NMR ($d_6$-DMSO, 100 MHz): 48.5, 66.5, 110.6, 115.4, 119.6, 125.3, 129.8, 150.6, 161.2.

Example 6

Methyl 4-(2-thioxo-2,3-dihydro-1H-imidazol-4-yl)benzoate (Method A)

$^1$H NMR ($d_6$-DMSO, 400 MHz): 3.85 (s, 3H, $OCH_3$); 7.63 (s, 1H, CH); 7.82 (d, 2H, J=8 Hz, ArH); 7.94 (d, 2H, J=8 Hz, ArH); 12.3 (s, 1H, NH); 12.7 (s, 1H, NH).

$^{13}$C NMR ($d_6$-DMSO, 100 MHz): 55.8, 118.2, 127.4, 131.3, 131.6, 133.4, 136.4, 166.2, 169.4.

Example 7

4-(4-(Hydroxymethyl)phenyl)-1,3-dihydroimidazole-2-thione (Method A)

A suspension of 318 mg (1.36 mmol, 1 eq) of methyl 4-(2-thioxo-2,3-dihydro-1H-imidazol-4-yl)benzoate (Example 6) in 5 ml of tetrahydrofuran is slowly added to a suspension of 120 mg (5.6 mmol, 4 eq) of lithium borohydride in 3 ml of tetrahydrofuran at ambient temperature.

The reaction mixture is stirred at 70° C. for 8 hours. The reaction mixture is poured onto ice-cold water and then extracted with ethyl acetate. The residue is chromatographed on silica gel (dichloromethane/methanol 9/1). 100 mg of 4-(4-(hydroxymethyl)phenyl)-1,3-dihydroimidazole-2-thione are obtained.

Yield=36%.

$^1$H NMR (d$_6$-DMSO, 400 MHz): 4.54 (s, 2H, CH$_2$); 5.26 (s, 1H, OH); 7.33 (d, 2H, J=8 Hz, ArH); 7.42 (s, 1H, CH); 7.68 (d, 2H, J=8 Hz, ArH); 12.2 (s, 1H, NH); 12.6 (s, 1H, NH).

$^{13}$C NMR (d$_6$-DMSO, 100 MHz): 63.0, 112.3, 124.4, 127.3, 129.5, 142.1, 162.0.

Method B.

Example 8

4-(4-(Trifluoromethoxy)phenyl)-1,3-dihydroimidazole-2-thione (Method B)

2-Amino-1-(4-(trifluoromethoxy)phenyl)ethanone hydrochloride 325 mg (3.4 mmol, 1.2 eq) of sodium diformylamide are added to a solution of 800 mg (2.82 mmol, 1 eq) of 4-(trifluoromethoxy)phenacyl bromide in 10 ml of acetonitrile. The reaction mixture is stirred at ambient temperature for 3 days. The reaction mixture is filtered and then the solvents are evaporated. The residue is dissolved in 9 ml of a 1M solution of hydrochloric acid in ethanol and then stirred at ambient temperature for 16 hours. After disappearance of the starting material, 2-amino-1-(4-(trifluoromethoxy)phenyl)ethanone hydrochloride is precipitated by the addition of diethyl ether. 490 mg of white powder are collected.

Yield=68%.

$^1$H NMR (d$_6$-DMSO, 400 MHz): 4.61 (s, 2H, CH$_2$); 7.58 (d, 2H, J=8 Hz, ArH); 8.16 (d, 2H, J=8 Hz, ArH); 8.51 (s, 3H, NH$_3$).

4-(4-(Trifluoromethoxy)phenyl)-1,3-dihydroimidazole-2-thione 490 mg (1.89 mmol, 1 eq) of 2-amino-1-(4-(trifluoromethoxy)phenyl)ethanone hydrochloride and 320 mg (8.62 mmol, 4.5 eq) of potassium isothiocyanate are dissolved in 5 ml of water in the presence of 1 ml of a 2M hydrochloric acid solution. The reaction mixture is stirred at 100° C. for 16 hours. 320 mg (8.62 mmol, 4.5 eq) of potassium isothiocyanate are added and the reaction mixture is stirred at 100° C. for 16 hours. The medium is filtered and then the solid is washed with water. 320 mg of 4-(4-(trifluoromethoxy)phenyl)-1,3-dihydroimidazole-2-thione are collected.

Yield=64%

$^1$H NMR (d$_6$-DMSO, 400 MHz): 7.36 (d, 2H, J=8 Hz, ArH); 7.44 (s, 1H, CH); 7.75 (d, 2H, J=8 Hz, ArH); 12.2 (s, 1H, NH); 12.7 (s, 1H, NH).

$^{13}$C NMR (d$_6$-DMSO, 100 MHz): 113.6, 120.5 (d, J=260 Hz), 122.0, 126.1, 128.2, 128.3, 147.6, 162.6.

The following compounds were obtained analogously to Example 8:

Example 9

4-(4-(Difluoromethoxy)phenyl)-1,3-dihydroimidazole-2-thione (Method B)

$^1$H NMR (d$_6$-DMSO, 400 MHz): 7.13 (d, 2H, J=8 Hz, ArH); 7.20 (t, J=74 Hz, 1H, CHF$_2$); 7.32 (s, 1H, CH); 7.66 (d, 2H, J=8 Hz, ArH); 12.1 (s, 1H, NH); 12.5 (s, 1H, NH).

$^{13}$C NMR (d$_6$-DMSO, 100 MHz): 112.7, 116.7 (t, J=255 Hz), 119.5, 125.9, 128.5, 150.3, 162.3.

Example 10

4-(3-Butoxyphenyl)-1,3-dihydroimidazole-2-thione (Method B)

$^1$H NMR (d$_6$-DMSO, 400 MHz): 0.95 (t, 3H, J=7 Hz, CH$_3$); 1.44 (m, 4H, CH$_2$); 1.69 (m, 4H, CH$_2$); 4.00 (t, 2H, J=7 Hz, CH$_2$); 6.80 (d, 1H, J=8 Hz, ArH); 7.23 (m, 3H, ArH & CH); 7.44 (s, 1H, ArH); 12.1 (s, 1H, NH); 12.5 (s, 1H, NH).

$^{13}$C NMR (d$_6$-DMSO, 100 MHz): 14.2, 19.2, 31.2, 67.6, 109.9, 112.8, 114.2, 116.5, 129.4, 130.0, 130.3, 159.6, 162.0.

Example 11

4-(3-Methoxyphenyl)-1,3-dihydroimidazole-2-thione (Method B)

$^1$H NMR (d$_6$-DMSO, 400 MHz): 3.79 (s, 1H, CH$_3$); 6.82 (d, 1H, J=8 Hz, ArH); 7.23 (m, 3H, ArH & CH); 7.44 (s, 1H, ArH); 12.1 (s, 1H, NH); 12.6 (s, 1H, NH).

$^{13}$C NMR (d$_6$-DMSO, 100 MHz): 55.6, 109.5, 113.0, 113.7, 116.7, 129.3, 130.0, 130.3, 160.1, 162.0.

Example 12

4-(2-Methylphenyl)-1,3-dihydroimidazole-2-thione (Method B)

$^1$H NMR (d$_6$-DMSO, 400 MHz): 2.34 (s, 3H, CH$_3$); 7.00 (s, 1H, CH); 7.23 (m, 3H, 3ArH); 7.40 (d, 1H, J=8 Hz, ArH); 12.1 (s, 1H, NH); 12.3 (s, 1H, NH).

$^{13}$C NMR (d$_6$-DMSO, 100 MHz): 21.3, 114.7, 126.4, 128.2, 128.3, 128.4, 128.5, 131.2, 135.5, 161.5.

Example 13

4-(2-Methoxyphenyl)-1,3-dihydroimidazole-2-thione (Method B)

$^1$H NMR (d$_6$-DMSO, 400 MHz): 3.89 (s, 3H, OCH$_3$); 6.97 (t, 1H, J=8 Hz, ArH); 7.09 (d, 1H, J=8 Hz, ArH); 7.23 (s, 1H, CH); 7.27 (t, 1H, J=8 Hz, ArH); 7.74 (d, 1H, J=8 Hz, ArH); 12.2 (s, 1H, NH); 12.4 (s, 1H, NH).

$^{13}$C NMR (d$_6$-DMSO, 100 MHz): 55.8, 111.8, 115.6, 116.4, 125.8, 120.9, 126.0, 128.7, 155.7, 161.5.

Example 14

4-(3-Methylphenyl)-1,3-dihydroimidazole-2-thione (Method B)

$^1$H NMR (d$_6$-DMSO, 400 MHz): 2.30 (s, 3H, CH$_3$); 7.06 (d, 1H, J=8 Hz, ArH); 7.25 (t, 1H, J=8 Hz, ArH); 7.35 (s, 1H, CH); 7.45 (d, 1H, J=8 Hz, ArH); 7.50 (s, 1H, ArH); 12.1 (s, 1H, NH); 12.6 (s, 1H, NH).

$^{13}$C NMR (d$_6$-DMSO, 100 MHz): 21.5, 112.5, 121.5, 124.9, 128.4, 128.7, 129.1, 129.6, 138.4, 162.1.

Example 15

4-(3-(Trifluoromethoxy)phenyl)-1,3-dihydroimidazole-2-thione (Method B)

$^1$H NMR (d$_6$-DMSO, 400 MHz): 7.22 (d, 1H, J=8 Hz, ArH); 7.49 (t, 1H, J=8 Hz, ArH); 7.57 (s, 1H, CH); 7.69 (m, 2H, ArH); 12.1 (s, 1H, NH); 12.7 (s, 1H, NH).

$^{13}$C NMR (d$_6$-DMSO, 100 MHz).

Example 16

3-(2-Thioxo-2,3-dihydro-1H-imidazol-4-yl)benzonitrile $^1$H NMR (d$_6$-DMSO, 400 MHz): 7.58 (m, 2H, ArH); 7.71 (d, 1H, J=8 Hz, ArH); 8.00 (d, 1H, J=8 Hz, ArH); 8.18 (s, 1H, CH); 12.3 (s, 1H, NH); 12.7 (s, 1H, NH).
$^{13}$C NMR (d$_6$-DMSO, 100 MHz): 112.5, 114.4, 119.0, 127.5, 127.6, 128.5, 130.0, 130.5, 130.9, 162.8.

Example 17

4-(4-Isobutylphenyl)-1,3-dihydroimidazole-2-thione (Method B)

$^1$H NMR (d$_6$-DMSO, 400 MHz): 0.81 & 0.82 (2s, 6H, 2 CH$_3$); 1.79 (m, 1H, CH); 2.39 (d, 2H, J=7 Hz, CH$_2$); 7.11 (d, 2H, J=8 Hz, ArH); 7.29 (s, 1H, CH); 7.53 (d, 2H, J=8 Hz, ArH); 12.1 (s, 1H, NH); 12.5 (s, 1H, NH).
$^{13}$C NMR (d$_6$-DMSO, 100 MHz): 22.6, 30.0, 44.7, 112.0, 124.2, 126.3, 129.6, 129.8, 140.8, 161.9.

Example 18

4-(4-Ethylphenyl)-1,3-dihydroimidazole-2-thione (Method B)

$^1$H NMR (d$_6$-DMSO, 400 MHz): 1.15 (t, 3H, J=7 Hz, CH$_3$); 2.56 (q, 2H, J=7 Hz, CH$_2$); 7.19 (d, 2H, J=8 Hz, ArH); 7.31 (s, 1H, CH); 7.56 (d, 2H, J=8 Hz, ArH); 12.1 (s, 1H, NH); 12.5 (s, 1H, NH).
$^{13}$C NMR (d$_6$-DMSO, 100 MHz): 15.9, 28.3, 111.0, 124.4, 126.3, 128.6, 129.6, 143.4, 161.9.

Example 19

4-(3-Ethylphenyl)-1,3-dihydroimidazole-2-thione (Method B)

$^1$H NMR (d$_6$-DMSO, 400 MHz): 1.19 (t, 3H, J=7 Hz, CH$_3$); 2.59 (q, 2H, J=7 Hz, CH$_2$); 7.09 (d, 1H, J=8 Hz, ArH); 7.26 (t, 1H, J=8 Hz, ArH); 7.37 (s, 1H, CH); 7.45 (d, 1H, J=8 Hz, ArH); 7.55 (s, 1H, ArH), 12.1 (s, 1H, NH); 12.5 (s, 1H, NH).
$^{13}$C NMR (d$_6$-DMSO, 100 MHz): 15.8, 28.6, 112.5, 121.7, 123.8, 127.3, 128.7, 129.2, 129.7, 144.8, 162.0.

Example 20

4-(3,4-Dimethylphenyl)-1,3-dihydroimidazole-2-thione (Method B)

$^1$H NMR (d$_6$-DMSO, 400 MHz): 2.19 & 2.20 (2s, 6H, 2 CH$_3$); 7.11 (d, 1H, J=8 Hz, ArH); 7.28 (s, 1H, CH); 7.36 (d, 1H, J=8 Hz, ArH); 7.47 (s, 1H, ArH); 12.1 (s, 1H, NH); 12.5 (s, 1H, NH).
$^{13}$C NMR (d$_6$-DMSO, 100 MHz): 19.5, 19.9, 111.8, 121.8, 125.5, 126.3, 129.7, 130.3, 135.9, 137.0, 161.8.

Example 21

Tyrosinase Activity Inhibition Assay

The activity of the inhibitors is measured starting from a lysate of B16F1 cells (murine melanoma line). In the presence of the L-tyrosine substrate, the tyrosinase present in these cells catalyses the hydroxylation of L-tyrosine to give L-DOPA and then the oxidation of the L-DOPA to give dopaquinone. In the presence of MBTH (3-methyl-2-benzothiazolinone hydrazone), the dopaquinone is trapped so as to form a pink complex which absorbs at 520 nm.

The B16F1 cells are cultured in DMEM medium+10% foetal calf serum+10$^{-9}$ M α-MSH for 4 days at 37° C. under 7% CO$_2$. They are treated with trypsin, washed with PBS, counted and pelleted. The pellet is taken up at 10$^7$ cells/ml in lysis buffer (10 mM sodium phosphate, pH 6.8-1% Igepal) and the suspension is treated with ultrasound for 10 seconds. After centrifugation for 30 minutes at 4000 rpm, the supernatant obtained constitutes the cell lysate used as tyrosinase source in the enzymatic assay.

The assays are carried out in duplicate in 384-well plates in a total volume of 50 μl. Each well contains:

40 μl of solution containing 1.25 mM L-tyrosine, 6.25 μM L-DOPA (cofactor) and 3.75 mM MBTH in buffer B (62.25 mM sodium phosphate, pH 6.8-2.5% dimethylformamide), 5 μl of inhibitor diluted in DMSO, 5 μl of cell lysate diluted to ½ in 50 mM Tris HCl buffer, pH 7.5.

The plate is incubated at 37° C. and a spectrophotometric reading is carried out at 520 nm after incubating for 6 hours. To avoid any possible absorption of the products, the system uses corrected absorbance (absorbance at time 6 h−absorbance at time zero).

The inhibitors are assayed in terms of dose-response so as to calculate an IC$_{50}$ (dose which inhibits 50% of the enzymatic activity).

Several internal controls are added to each experiment:

control for 100% activity: the 5 μl of inhibitor are replaced with 5 μl of DMSO, control for 50% activity: the 5 μl of inhibitor are replaced with 5 μl of phenylthiourea at 300 μM in DMSO, control for 0% activity: the L-tyrosine substrate is replaced with buffer B.

The results obtained for the compounds of the invention are presented in Table A:

TABLE A

| Name | Structure | Tyrosine hydroxylase/Dopa oxidase IC$_{50}$ (μM) |
|---|---|---|
| Compound 3 | (structure) | 0.2 |
| Compound 7 | (structure) | 0.3 |

TABLE A-continued

| Name | Structure | Tyrosine hydroxylase/Dopa oxidase IC$_{50}$ (μM) |
|---|---|---|
| Compound 9 | | 0.4 |
| Compound 11 | | 1.4 |

Example 22

Formulations

In this example, various specific formulations based on the compounds according to the invention have been illustrated.

Topically:

(a) Ointment:

| | |
|---|---|
| Compound 1 | 10.020 g |
| Isopropyl myristate | 81.700 g |
| Liquid petrolatum | 9.100 g |
| Silica ("Aerosil 200") | 9.180 g |

(b) Ointment:

| | |
|---|---|
| Compound 6 | 0.300 g |
| White petrolatum, pharmaceutical grade | q.s. for 100 g |

(c) Nonionic Water-in-Oil Cream:

| | |
|---|---|
| Compound 1 | 0.100 g |
| Mixture of emulsive lanolin alcohols, of waxes and of oils ("Anhydrous eucerin") | 39.900 g |
| Methyl para-hydroxybenzoate | 0.075 g |
| Propyl para-hydroxybenzoate | 0.075 g |
| Sterile demineralized water | q.s. for 100 g |

(d) Lotion:

| | |
|---|---|
| Compound 6 | 0.100 g |
| Polyethylene glycol (PEG 400) | 69.900 g |
| 95% Ethanol | 30.000 g |

(e) Hydrophobic Ointment:

| | |
|---|---|
| Compound 2 | 0.300 g |
| Isopropyl myristate | 36.400 g |
| Silicone oil ("Rhodorsil 47 V 300") | 36.400 g |
| Beeswax | 13.600 g |
| Silicone oil ("Abil 300 000 cst", marketed by Goldschmidt) | q.s. for 100 g |

(f) Nonionic Oil-in-Water Cream:

| | |
|---|---|
| Compound 4 | 1.000 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | q.s. for 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 4-phenylimidazole-2-thione tyrosinase inhibiting compound having the formula (I):

(I)

in which:
a) when R2=H, then R1 is:
  a $C_2$-$C_7$ alkyl radical, with the proviso that R1 cannot be isopropyl, n-propyl or tert-butyl,
  a hydroxymethyl, trifluoromethoxy or difluoromethoxy radical,
  a $C_3$-$C_7$ cycloalkyl radical, with the proviso that one of the carbon atoms of the ring may optionally be replaced by an oxygen or sulfur atom,
  a $C_4$-$C_9$ cycloalkylalkyl radical,
  a morpholinyl, thiomorpholinyl, piperazinyl or N-methylpiperazinyl group,
  a carboxyl substituent,
  a ($C_1$-$C_4$ alkoxy)carbonyl group, or
  a $C_2$-$C_6$ alkoxy radical, with the proviso that R1 cannot be n-butoxy;

b) when R1=H, then R2 is:
  a $C_1$-$C_7$ alkyl radical,
  a trifluoromethoxy, difluoromethoxy or cyano radical,
  a $C_3$-$C_7$ cycloalkyl radical, with the proviso that one of the carbon atoms of the ring may optionally be replaced by an oxygen or sulfur atom,
  a $C_4$-$C_9$ cycloalkylalkyl radical,
  a ($C_1$-$C_4$ alkoxy)carbonyl radical,
  a $C_1$-$C_6$ alkoxy radical, with the proviso that R2 cannot be n-propoxy;
c) and, when R2 is in the ortho position with respect to R1, then R1 and R2, which may be identical or different, are each a $C_1$-$C_5$ alkyl radical or together form a 5- or 6-sided hydrocarbon ring, in which 1 or 2 carbon atom(s) are optionally replaced by 1 or 2 oxygen atom(s),
or a salt or tautomeric form thereof.

2. A compound as defined by claim 1, wherein, when R2 is in the ortho position with respect to R1, then R1 and R2, which may be identical or different, are each a $C_1$-$C_5$ alkyl radical or together form a 5- or 6-sided hydrocarbon ring.

3. A compound as defined by claim 1, in the form of a salt formed with an acid selected from among inorganic acids and organic acids.

4. A compound as defined by claim 1, wherein R2=H and R1 is selected from the group consisting of cyclopropyl, cyclobutyl, cyclopentyl, cyclohexyl and cycloheptyl radicals.

5. A compound as defined by claim 1, wherein R2 is a hydrogen atom and R1 is a $C_2$-$C_7$ alkyl radical, with the proviso that R1 cannot be isopropyl, n-propyl or tert-butyl; or R1 is a $C_3$-$C_7$ cycloalkyl radical or a $C_4$-$C_9$ cycloalkylalkyl radical.

6. A compound as defined by claim 1, wherein R1 is a hydrogen atom and R2 is a $C_1$-$C_7$ alkyl radical or a $C_3$-$C_7$ cycloalkyl radical or a $C_4$-$C_9$ cycloalkylalkyl radical.

7. A compound as defined by claim 1, selected from the group consisting of:
  4-(4-pentylphenyl)-1,3-dihydroimidazole-2-thione;
  4-(3-carboxyphenyl)-1,3-dihydroimidazole-2-thione;
  4-(4-carboxyphenyl)-1,3-dihydroimidazole-2-thione;
  4-(4-cyclohexylphenyl)-1,3-dihydroimidazole-2-thione;
  4-(4-(morpholin-4-yl)phenyl)-1,3-dihydroimidazole-2-thione;
  methyl 4-(2-thioxo-2,3-dihydro-1H-imidazol-4-yl)benzoate;
  4-(4-(hydroxymethyl)phenyl)-1,3-dihydroimidazole-2-thione;
  4-(4-(trifluoromethoxy)phenyl)-1,3-dihydroimidazole-2-thione;
  4-(4-(difluoromethoxy)phenyl)-1,3-dihydroimidazole-2-thione;
  4-(3-butoxyphenyl)-1,3-dihydroimidazole-2-thione;
  4-(3-methoxyphenyl)-1,3-dihydroimidazole-2-thione;
  4-(2-methylphenyl)-1,3-dihydroimidazole-2-thione;
  4-(2-methoxyphenyl)-1,3-dihydroimidazole-2-thione;
  4-(3-methylphenyl)-1,3-dihydroimidazole-2-thione;
  4-(3-(trifluoromethoxy)phenyl)-1,3-dihydroimidazole-2-thione;
  3-(2-thioxo-2,3-dihydro-1H-imidazol-4-yl)benzonitrile;
  4-(4-isobutylphenyl)-1,3-dihydroimidazole-2-thione;
  4-(4-ethylphenyl)-1,3-dihydroimidazole-2-thione;
  4-(3-ethylphenyl)-1,3-dihydroimidazole-2-thione;
  4-(3,4-dimethylphenyl)-1,3-dihydroimidazole-2-thione;
  4-(4-cyclopentylphenyl)-1,3-dihydroimidazole-2-thione;
  4-(3-cyclopentylphenyl)-1,3-dihydroimidazole-2-thione;
  4-(3-cyclohexylphenyl)-1,3-dihydroimidazole-2-thione;
  4-(5,6,7,8-tetrahydronaphth-2-yl)-1,3-dihydroimidazole-2-thione;
  4-(indan-5-yl)-1,3-dihydroimidazole-2-thione;
  4-(2,3-dihydrobenzofuran-5-yl)-1,3-dihydroimidazole-2-thione;
  4-(2,3-dihydrobenzo[1,4]dioxin-6-yl)-1,3-dihydroimidazole-2-thione;
  4-(benzo[1,3]dioxol-5-yl)-1,3-dihydroimidazole-2-thione;
  4-[4-(tetrahydropyran-4-yl)phenyl]-1,3-dihydroimidazole-2-thione;
  4-[3-(tetrahydropyran-4-yl)phenyl]-1,3-dihydroimidazole-2-thione;
  4-(3,4-diethylphenyl)-1,3-dihydroimidazole-2-thione;
  4-(3-ethyl-4-isopropylphenyl)-1,3-dihydroimidazole-2-thione;
  4-(4-ethyl-3-isobutylphenyl)-1,3-dihydroimidazole-2-thione; and
  4-(3,4-diethylphenyl)-1,3-dihydroimidazole-2-thione hydrochloride.

8. A regime or regimen for the treatment of hyperpigmentary disorders, comprising topically applying onto the skin, mucous membranes and/or superficial body growths of an individual in need of such treatment, a thus effective amount of at least one compound having the formula (I):

in which:
a) when R2=H, then R1 is:
  a $C_2$-$C_7$ alkyl radical, with the proviso that R1 cannot be isopropyl, n-propyl or tert-butyl,
  a hydroxymethyl, trifluoromethoxy or difluoromethoxy radical,
  a $C_3$-$C_7$ cycloalkyl radical, with the proviso that one of the carbon atoms of the ring may optionally be replaced by an oxygen or sulfur atom,
  a $C_4$-$C_9$ cycloalkylalkyl radical,
  a morpholinyl, thiomorpholinyl, piperazinyl or N-methylpiperazinyl group,
  a carboxyl substituent,
  a ($C_1$-$C_4$ alkoxy)carbonyl radical or
  a $C_2$-$C_6$ alkoxy radical, with the proviso that R1 cannot be n-butoxy;
b) when R1=H, then R2 is:
  a $C_1$-$C_7$ alkyl radical,
  a trifluoromethoxy, difluoromethoxy or cyano radical,
  a $C_3$-$C_7$ cycloalkyl radical, with the proviso that one of the carbon atoms of the ring may optionally be replaced by an oxygen or sulfur atom,
  a $C_4$-$C_9$ cycloalkylalkyl radical,
  a ($C_1$-$C_4$ alkoxy)carbonyl radical,
  a $C_1$-$C_6$ alkoxy radical, with the proviso that R2 cannot be n-propoxy;
c) and, when R2 is in the ortho position with respect to R1, then R1 and R2, which may be identical or different, are each a $C_1$-$C_6$ alkyl radical or together form a 5- or 6-sided hydrocarbon ring, with the proviso that 1 or 2 carbon atom(s) are optionally replaced by 1 or 2 oxygen atom(s),
or a salt or tautomeric form thereof;
formulated into a topically applicable, pharmaceutically/cosmetically acceptable vehicle therefor.

9. The regime or regime as defined by claim 8, wherein said hyperpigmentary disorders are selected from among melasma, chloasma, lentigines, senile lentigo, irregular hyperpigmentations related to photoaging, freckles, postinflammatory hyperpigmentations due to an abrasion and/or to a burn and/or to a scar and/or to a dermatosis and/or to a contact allergy, naevi, genetically determined hyperpigmentations, hyperpigmentations of metabolic or drug origin and melanomas.

10. A topically applicable pharmaceutical composition useful for the treatment of hyperpigmentary disorders, comprising at least one compound having the formula (I):

in which:
a) when R2=H, then R1 is:
a $C_2$-$C_7$ alkyl radical, with the proviso that R1 cannot be isopropyl, n-propyl or tert-butyl,
   a hydroxymethyl, trifluoromethoxy or difluoromethoxy radical,
   a $C_3$-$C_7$ cycloalkyl radical, with the proviso that one of the carbon atoms of the ring may optionally be replaced by an oxygen or sulfur atom,
   a $C_4$-$C_9$ cycloalkylalkyl radical,
   a morpholinyl, thiomorpholinyl, piperazinyl or N-methylpiperazinyl group,
   a carboxyl substituent,
   a ($C_1$-$C_4$ alkoxy)carbonyl radical or
   a $C_2$-$C_6$ alkoxy radical, with the proviso that R1 cannot be n-butoxy;
b) when R1=H, then R2 is:
   a $C_1$-$C_7$ alkyl radical,
   a trifluoromethoxy, difluoromethoxy or cyano radical,
   a $C_3$-$C_7$ cycloalkyl radical, with the proviso that one of the carbon atoms of the ring may optionally be replaced by an oxygen or sulfur atom,
   a $C_4$-$C_9$ cycloalkylalkyl radical,
   a ($C_1$-$C_4$ alkoxy)carbonyl radical,
   a $C_1$-$C_6$ alkoxy, with the proviso that R2 cannot be n-propoxy;
c) and, when R2 is in the ortho position with respect to R1, then R1 and R2, which may be identical or different, are each a $C_1$-$C_6$ alkyl radical or together form a 5- or 6-sided hydrocarbon ring, with the proviso that 1 or 2 carbon atom(s) are optionally replaced by 1 or 2 oxygen atom(s),
or a salt or tautomeric form thereof;
formulated into a topically applicable, pharmaceutically acceptable vehicle therefor.

11. The composition as defined by claim 10, wherein the concentration of compound of formula (I) ranges from 0.001% to 10% by weight, with respect to the total weight of the composition.

12. The composition as defined by claim 11, wherein the concentration of compound of formula (I) ranges from 0.01% to 5% by weight, with respect to the total weight of the composition.

13. A cosmetic composition comprising, formulated into a cosmetically acceptable vehicle, at least one compound of formula (I) as defined by claim 1.

14. The composition as defined by claim 13, wherein the concentration of compound of formula (I) ranges from 0.001% to 3% by weight, with respect to the total weight of the composition.

15. The regime or regimen as defined by claim 8, for treating signs of skin aging.

16. The regime or regimen as defined in claim 8, for body or hair hygiene.

* * * * *